United States Patent [19]

Cable et al.

[11] Patent Number: 4,685,903
[45] Date of Patent: Aug. 11, 1987

[54] EXTERNAL INFUSION PUMP APPARATUS

[75] Inventors: Vaughn P. Cable, Woodland Hills; Clyde K. Nason, Valencia; Gordon W. Culp, Van Nuys, all of Calif.

[73] Assignee: Pacesetter Infusion, Ltd., Sylmar, Calif.

[21] Appl. No.: 568,614

[22] Filed: Jan. 6, 1984

[51] Int. Cl.⁴ .............................................. A61M 37/00
[52] U.S. Cl. ............................ 604/154; 128/DIG. 12; 417/44; 604/151
[58] Field of Search ............... 604/154, 155, 151, 152, 604/153; 128/DIG. 12; 417/44, 45

[56] References Cited

U.S. PATENT DOCUMENTS

| | | | |
|---|---|---|---|
| 4,210,138 | 7/1980 | Jess et al. | 128/214 E |
| 4,351,332 | 9/1982 | Whitney et al. | 128/214 F |
| 4,360,019 | 11/1982 | Portner et al. | 128/213 R |
| 4,373,527 | 2/1983 | Fischell | 128/260 |
| 4,447,224 | 4/1984 | DeCant, Jr. et al. | 604/67 |
| 4,469,481 | 9/1984 | Kobayashi | 604/67 |

Primary Examiner—John F. Niebling
Assistant Examiner—William T. Leader
Attorney, Agent, or Firm—Leslie S. Miller; Bryant R. Gold; Wayne M. Kennard

[57] ABSTRACT

A programmable infusion pump apparatus having a power supply (4, 11), a first circuit (6) responsive to the and assisting the power supply (4), power generating circuit (8) for generating sufficient power to drive a pump drive mechanism (12), a power storage circuit (10) for storing the power generated by the power generating circuit (8), a sensing system (16) for sensing stored power levels and the condition of the power supply (11), a microprocessor (18); a plurality of actuators (24, 26, 28, 30) for display and changing parameter values stored in RAM of the microprocessor (18), a memory (34) operably connected to microprocessor (18); display screen (40) for displaying parameter values and other information concerning the apparatus and a tone transducer (22) for providing an audio output from the apparatus to indicate certain conditions.

20 Claims, 14 Drawing Figures

FIG. 13

EXTERNAL INFUSION PUMP APPARATUS

DESCRIPTION

1. Technical Field

The present invention relates to the field of fluid pumping apparatuses and their method of use. In particular, the present invention further relates to external infusion pump apparatuses and their method of use for providing accurate dosages of a fluid to a user.

2. Background Art

In the past, there have been various attempts to provide apparatuses which would be able to effectively simulate a malfunctioning body organ and provide certain fluids to the body for control of certain bodily functions. These apparatuses have been contemplated to be both internal and external. One of the largest areas for use of these apparatuses was to control the amount of insulin input required by a diabetic.

Without such devices, the diabetic had to rely on taking insulin injection at periodic intervals to control his disease. This required that the diabetic always carry around a hypodermic needle and a supply of insulin should the need arise that a dosage was required to control the disease.

This reaction type remedy caused the diabetic to take improper dosages of insulin to control his or her disease. It was rarely the case that the proper amounts of insulin were dispensed to the body as would be done by the insulin producing organ. Although insulin is being used by way of example, the same is true for other necessary fluids that are no longer supplied to the body in correct dosages because of a malfunctioning organ.

Previous apparatuses, used for supplying fluids to the body to replace or supplement the fluids provided by a malfunctioning organ, were reaction type devices and not intended to essentially simulate the improperly functioning organ.

The major drawback in reaction-type aparatuses was side effects to the user. In a particular case of a diabetic, there could be insulin shock because the body would not accept large dosages of insulin.

There have been various additional problems with previous apparatuses in their ability to change with the needs of the user. In most cases, if there was an automatic system, it would be set to provide a large volume of the required fluid to the body. Essentially, the apparatus would be hardwired to produce a certain output which would be unchanging. To prevent any problems with this type of system, it was always constructed such that there could be no changes in volumetric delivery made by the user. Any changes to be made in the prescription would have to be made by the physician or required the purchase and installation of a new system to handle this increased or decreased volumetric need.

Such apparatuses in the past were neither programmable nor able to be accessed and operated by the user. Since this was the case, it made the user extremely dependent upon the physician to take care of all of his needs in accordance with his or her specific physiological requirements. Because of the limited time that doctors have to see any particular user, it was difficult for the doctor to finalize the proper volumetric requirements for the user so as to prevent or minimize any side effects.

The present invention overcomes these and other problems as will be described subsequently.

SUMMARY OF INVENTION

The present invention is an external programmable infusion pumping apparatus or fluid delivery system for providing small accurate dosages of a required fluid to a user. This apparatus effectively simulates the periodic and volumetric requirements of a properly functioning human organ to provide a particular fluid to the body of the user.

The apparatus of the invention is attached to a catheter or other delivery system which is inserted subcutaneously for the delivery of the required body fluid to the user at periodic intervals.

The apparatus of the invention is extremely small in size and light in weight. It provides accurate dosages of a fluid to the user. The apparatus has analog and digital circuitry which works in conjunction with a microprocessor, external memory (external from the microprocessor) and an LCD display. The apparatus has incorporated therein circuitry for producing audio tones for indication of certain conditions or for warning the user of various problems that exist in the apparatus. Additionally, the apparatus has a pressure switch associated with a lead screw which will indicate when the fluid reservoir is empty or when there are problems with the pump apparatus that prevents the pumping of fluid from the reservoir.

The apparatus of the invention is programmable, as stated, and its programming can be changed by the physician or by the user. The apparatus has a series of actuator means in the form of buttons which are used to change the rate of volumetric output, concentration and maximum level of the pumped fluid, and further to display certain information. Additionally, whenever changes are made to the programming of the apparatus, of the new parameter values stored in the random access memory (RAM) of the microprocessor are displayed. The apparatus the invention also has protection circuits so that if there is some problem with the primary power source, the programming in the apparatus is maintained. This is also true when it is necessary to change primary power sources so that the user will not have to reprogram the apparatus after replacement of the primary power source.

An object of the invention is to provide a programmable fluid infusion pump apparatus that can accurately dispense specific volumes and/or rates of delivery of a desired fluid subcutaneously or otherwise to a user.

Another object of the invention is to provide a programmable fluid infusion pump apparatus having analog and digital circuitry means for accurately dispensing fluid to a user.

A still further object of the invention is to provide a programmable fluid infusion pump apparatus which has a means for protecting the programming of the apparatus when a primary power source fails or is removed.

A still further object of the invention is to provide a programmable fluid infusion pump apparatus having a microprocessor which is interactive with the analog and digital circuitry of the apparatus, displaying certain information about the status of the apparatus and further having an alarm means for indicating problems or certain conditions of the apparatus.

Another object of the invention is to provide a programmable fluid infusion pump apparatus which has charge storage means for storing generated power for driving a pump drive means.

3

A still further object of the invention is to provide a programmable fluid infusion pump apparatus with a plurality of actuator means for changing the programming of the apparatus of invention.

Another object of the invention is to provide a low level system for pumping a desired fluid to a user, and circuitry for protecting a power source from excessive power drain.

A further object of the invention is to provide a programmable fluid infusion pump apparatus having means for selectively engaging and disengaging an elongated threaded member.

Another object of the invention is to provide an electrically operated apparatus for driving a second apparatus mechanically.

A further object of the invention is to provide an apparatus which has the means for automatically changing the rate of delivery of a desired fluid to a user without user interaction.

An even further object of the invention is to provide an apparatus which has an alarm means to indicate when a fluid reservoir is empty or that fluid cannot be pumped from the reservoir because of a problem with the pump mechanism.

These and other objects of the invention will be described fully in subsequent paragraphs.

BEST MODE FOR CARRYING OUT THE INVENTION

Figure 1:
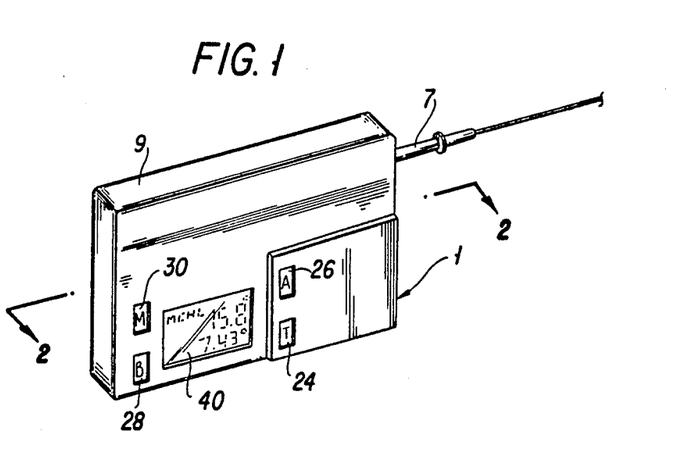
FIG. 1 shows an elevation view of the apparatus of the invention.
Figure 2:
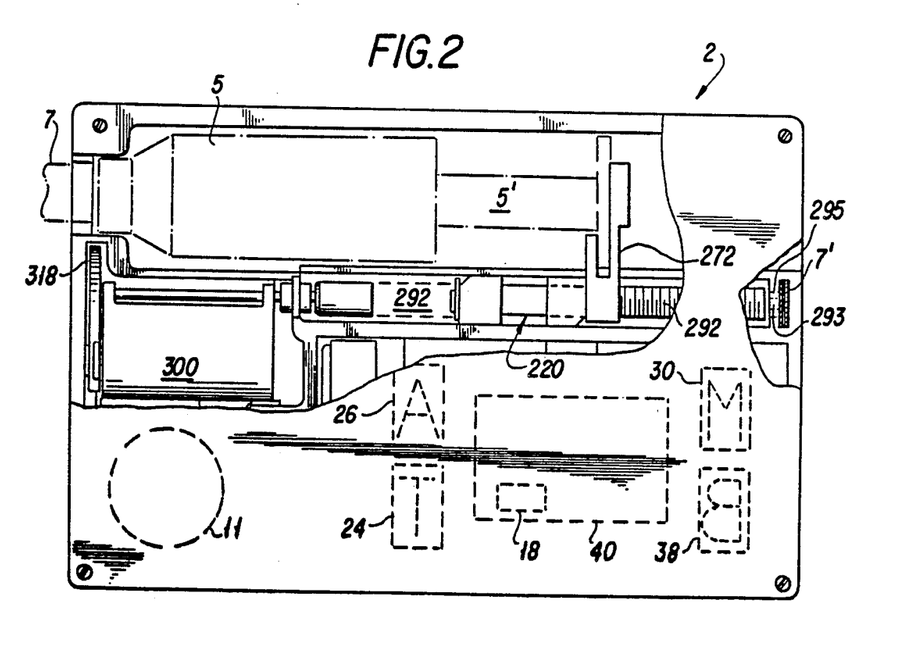
FIG. 2 shows a partially cut-away view of the apparatus of the invention along 2—2 of FIG. 1.

Referring to FIGS. 1 and 2, an elevated view and partial cut-away view of the apparatus of the invention is generally shown at 1 and 2, respectively. The apparatus has an outer casing 9, which houses microprocessor 18 and other circuitry, fluid reservoir 5, mechanical pump drive means 300, engagement/disengagement means 220 and primary power source 11. The fluid pumped from reservoir 5 is output through conduit 7 which is connected to a catheter or subcutaneous insertion point for input to the user. The actuator means, T button 24; A button 26; B button 28; and M button 30 are disposed through case 9 and used for changing program parameters within memory of the apparatus or displaying certain information on LCD 40. The relationship of some of the components of the apparatus of the invention is shown generally in FIG. 2.

Fluid in fluid reservoir 5 is dispensed through conduit 7 to the user as stated. The fluid is forced from the fluid reservoir 5 by plunger 5' shown in phantom in FIG. 2. The end of the plunger is engaged by pump driver 272 of engagement/disengagement means 220 which is disposed on lead screw 292. Lead screw 292 is driven by solenoid drive means 300. As solenoid drive means 300 causes rotation of ratchet wheel 318, lead screw 292 is rotated in a clockwise direction causing engagement/disengagement means 220 to move along lead screw 292 toward solenoid drive means 300, thereby forcing fluid from the reservoir into conduit 7.

Disposed at the distal end of lead screw 292 is high pressure switch 7'. The distal end of lead screw 292 has reduced portion 293 which has a rounded end. This reduced portion 293 is received through bearing 295 in an inside casing wall and the rounded end of reduced portion 293 contacts the high pressure switch 7'.

Once engagement/disengagement means 220 travels the length of lead screw 292 and all of the fluid has been pumped from fluid reservoir 5, plunger 5' will have traveled its full distance within fluid reservoir 5 and engagement/disengagement means 220 can no longer move in a direction toward pump drive means 300. Any further turning of lead screw 292 by pump drive means 300 will cause lead screw 292 to move in an axial direction toward pressure switch 7'. The rounded end of reduced portion 293 will be driven into high pressure switch 7' causing the switch to close. The appropriate alarm condition will be set.

Switch 7' will also be closed if plunger 5' becomes fouled and cannot be moved into fluid reservoir 5. In this case, lead screw 292 will again be driven toward high pressure switch 7' and the switch will be closed as stated. Again the appropriate alarm condition will be set.

Figure 3:
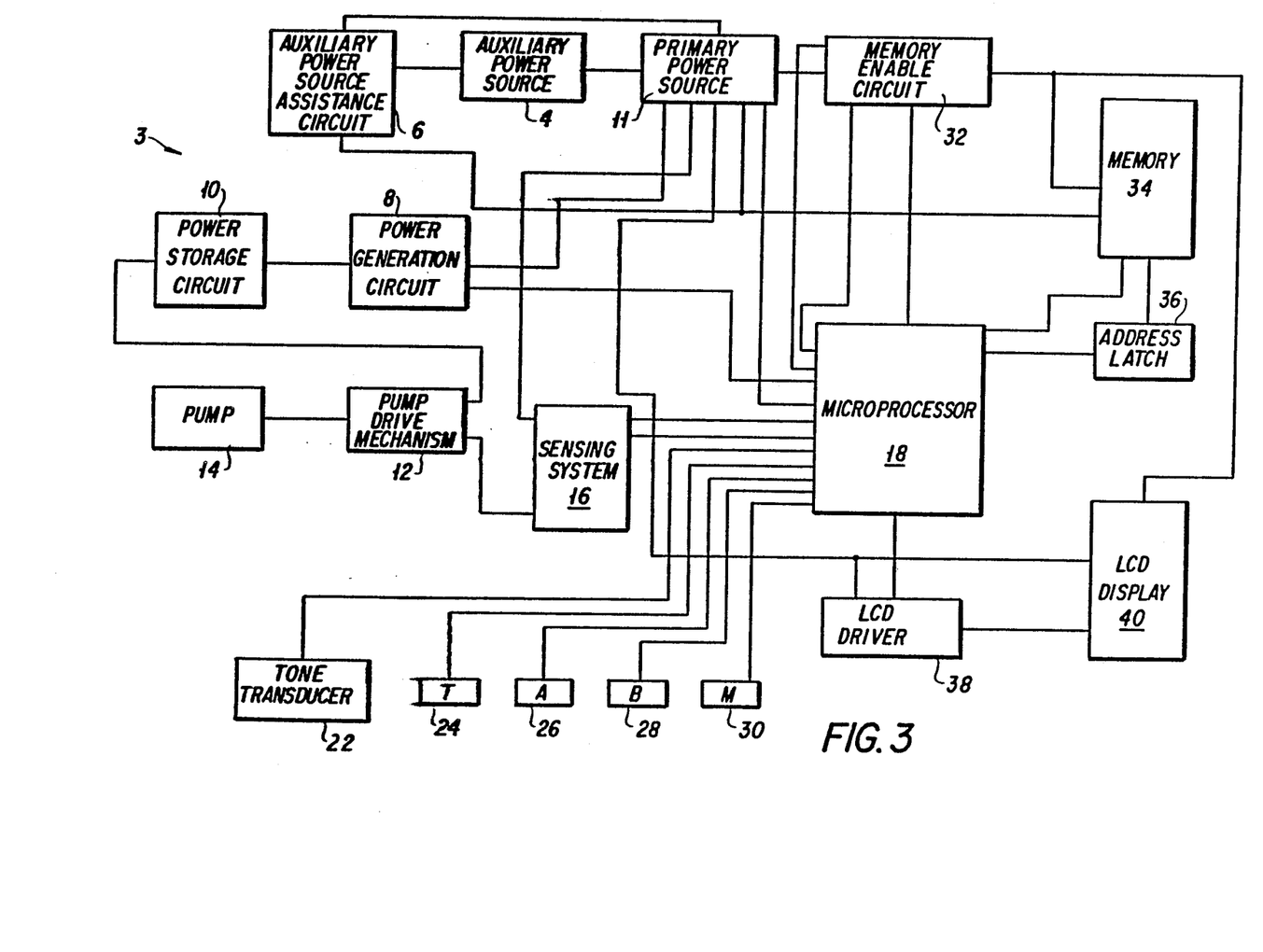
FIG. 3 is a block diagram of the apparatus of the invention.

Referring to FIG. 3, a block diagram of the apparatus of the invention is generally shown at 3. The main control means for operation of the apparatus of invention is microprocessor 18. The other components of the apparatus are connected to microprocessor 18 serving either input, output or memory functions.

The apparatus in general is powered by primary power source 11. Primary power source 11 usually consists of three 1.5 volt silver oxide batteries connected in series providing approximately 4.5 volts to power the system. Auxiliary power source 4, which is connected to auxiliary power source assistance circuit 6 is used in two situations. The first situation is when primary power source 11 falls below a certain voltage level below which the primary power source can no longer adequately power the apparatus. The second situation is when the primary power source is being replaced. In each case auxiliary power source 4 provides enough voltage to the apparatus to maintain the RAM of microprocessor 18 so that programming is not lost.

Auxiliary power source assistant circuit 6 is connected between the auxiliary power source and the system power supply line. The main purpose of this circuit is to provide a voltage to put the apparatus in a sleep state and supply enough voltage to maintain RAM of microprocessor 18.

The primary power source has means connected to all of the operable components of the apparatus. The auxiliary power source on the other hand is so situated in the circuit that it will provide the power to the entire apparatus but the apparatus is in a sleep state so power is provided to maintain RAM and not generally to the apparatus to make it operable.

Power generation circuit 8 is connected to primary power source 11 and microprocessor 18 and when powered, generates the proper power levels for driving pump drive mechanism 12 for operating pump 14. Power generation circuit 8 is disposed between primary power source 8 and power storage circuit 10.

Power storage circuit 10 receives the output from power generation circuit 8. A charge is built up and stored in circuit 10 until a predetermined voltage level is reached, at which time the power generation circuit is turned off. This voltage is stored in circuit 10 until it is delivered to pump drive mechanism 12.

Sensing system 16 is connected to primary power source 11, pump drive mechanism 12 and microprocessor 18. Sensing system 16 is used for two purposes. First, it senses when the primary power source voltage falls below a predetermined level, and second it senses when the storage circuit is charged to a certain voltage level. In conjunction with sensing the conditions of the storage circuit, it senses when voltage has been delivered from power storage 10 circuit to pump drive mechanism 12. Sensing system 16 inputs its sensed conditions to microprocessor 18 for carrying out the necessary internal apparatus functions indicative of the conditions that are sensed.

The operating software subroutines for operation of the apparatus are stored in a read only memory (ROM) 34. This memory is connected to microprocessor 18, address latch 36, power source 11, and memory enable means 32. The other memory of the apparatus is the RAM of microprocessor 18 which stores the present programming parameters for operation of the apparatus.

Once the proper parameter is in RAM, the apparatus will function in accordance with these parameters. Microprocessor 18 acts on these parameters stored in RAM and processes them in the subroutines stored in memory 34.

An oscillator internal to microprocessor 18 uses a 32768 Hz crystal which is divided down and provides proper clock timing for the apparatus of invention.

In order to display certain information, microprocessor 18 is connected to LCD driver 38 which in turn provides discrete outputs to LCD 40. By proper actuation of either T button 24; A button 26; B button 28; and/or M button 30 or combinations thereof, LCD 40 will display the desired information.

An additional feature of the apparatus is that tone transducer 22 provides audio tones to indicate certain alarm conditions or to indicate the occurrence of certain functions.

Figure 4:
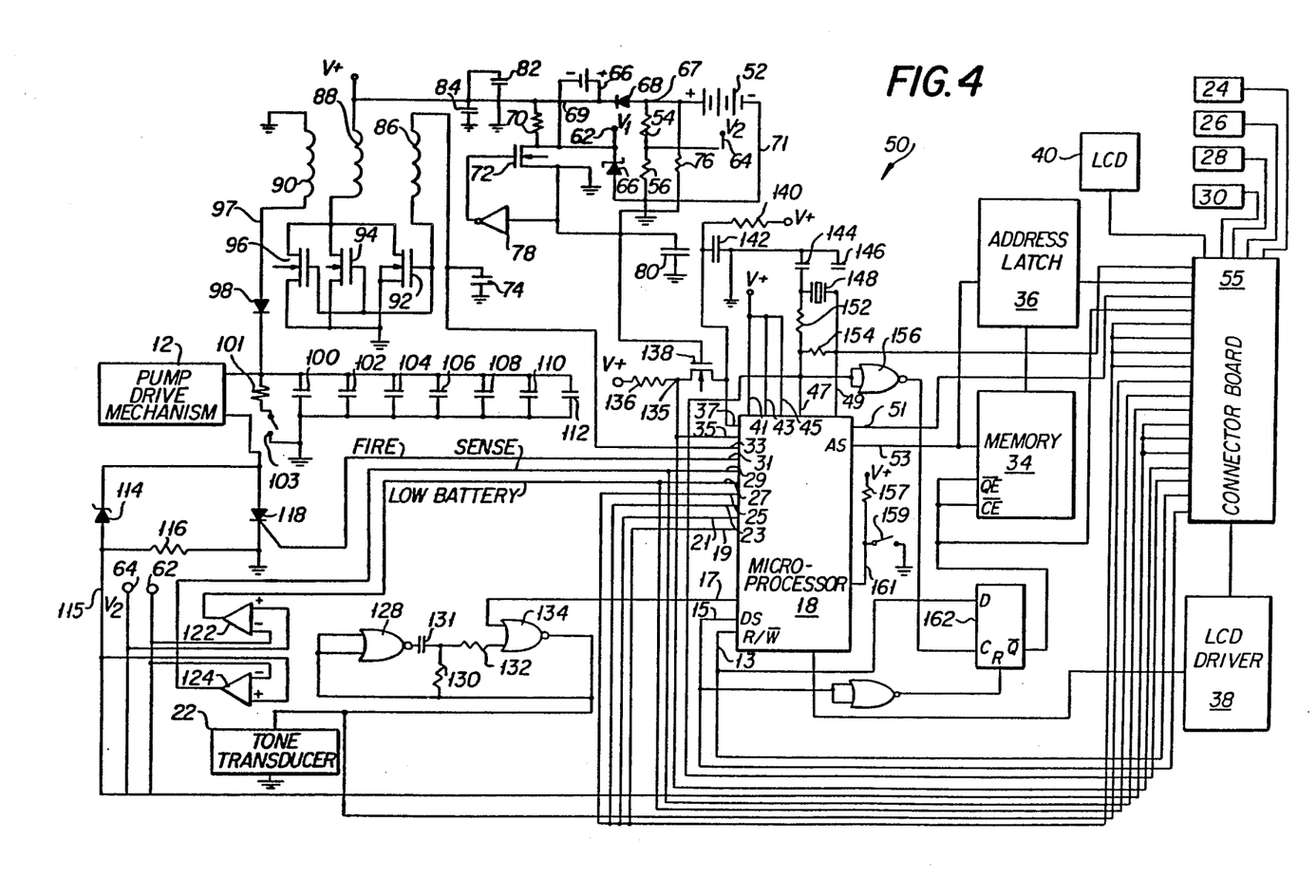
FIG. 4 shows the schematic diagram of the apparatus of the invention.

Referring to FIG. 4, analog circuitry, digital circuitry and certain components of the apparatus of invention are generally shown at 50. The apparatus is powered by primary power source 52.

The auxiliary power source is battery 60. This battery is a 3.1 volt lithium battery. The two power sources are so situated that the anodes or positive terminals of primary source 52 and auxiliary source 60 are connected to each other through a diode 68 on V+ line 69. When primary power source 52 is present, diode 68 is forward biased in the direction of auxiliary power source 60 on V+ line 69. This reverse biases Schottky diode 66 taking auxiliary power source 60 out of the circuit. The unique utilization of these two power sources will be described subsequently.

Primary power source 52 is used for generating the necessary voltage for operation of the apparatus. Auxiliary power source 60 is used for supplying voltage to RAM of microprocessor 18 when, for some reason, primary power source 52 is missing or inoperable. Associated with these two power sources are reference voltages V-1, 62 and V-2, 64 which are used in various places throughout the apparatus. A description of these reference voltages will follow in this disclosure.

When the primary power source 52 is present, diode 68 is forward biased as stated. When this is the case, there is approximately a 0.5 voltage drop across diode 68 and diode 66 is reversed biased. Therefore, the resultant voltage at V-1, when source 52 is present, is 4.5 volts minus the 0.5 volt drop across diode 68 and minus the voltage of auxiliary power source, 60 which is 3.1 volts. So, V-1, 62 will be approximately 0.9 volts.

Schottky diode 66 has its anode connected to the cathode of battery 52. The cathode is effectively at a zero voltage. Since V-1 is at 0.9 volts, this verifies Schottky diode 66 is reversed biased. V-1 will remain at 0.9 volts as long as source 52 is present. Schottky diode 66 will remain reversed biased as long as V-1, 62 has a positive value.

Voltage V-2, 64 is a divided down voltage of primary power source 52. The voltage of V-2 is dependent on the relationship of resistors 54 and 56. As will be explained, the V-2 reference voltage has an effective positive value only when primary power source 52 is in the circuit, otherwise it is near zero volts.

When primary power source 52 is removed, the only power source is auxiliary power source 60, the 3.1 volt lithium battery. When this is the case, diode 68 is reversed biased. The direction of current flow is from the anode of power source 60 to the circuit and back through ground through Schottky diode 66 to the cathode of battery 60. By this method, Schottky diode 66 is forward biased. Because of the current flow, the voltage at V-1, 62 will be one Schottky diode voltage drop, which is approximately 0.3 volts below common reference voltage (zero volts) on line 71. Also, since primary power source 52 is not in the circuit V-2, 64 is at or near zero volts.

When primary power source 52 is removed and auxiliary power source 60 provides the voltage to V+ line 69, this is sensed by microprocessor 18. When this takes place, microprocessor 18 will put the apparatus in a sleep state. When the apparatus is in this state, the bit pattern of RAM of microprocessor 18 is maintained.

In order to assist the auxiliary power source 60, capacitor 84 depletes its charge to V+ line 69. Also the action of inverter 78 and FET 72 and capacitor 74 assists in elevating the effective supply voltage to the apparatus.

In this case, the anode voltage of primary power source 52 is considered a logic "1" value and the cathode voltage is a logic "0" value. When primary power source 52 is present, the input to inverter 78 is a logic "1" value which causes the output of inverter 78 to assume a logic "0" value. This logic "0" value is input to the gate of field effect transistor (FET) 72, rendering it in an off condition. When primary power source 52 is removed, the input to inverter 78 is a logic "0" value, so, the output of inverter will assume a logic "1" value, which is input to the gate of FET 72 and turns it on. When this FET is turned on, it will cause shorting of the voltage at V-1 to ground. This will essentially short Schottky diode 66 to ground lessening the effect of the voltage drop across the Schottky diode. The voltage drop will change from a 0.3 volt drop to a 0.1 volt drop. This effectively adds 0.2 volts to the circuit on V+ line 69.

When the primary power source is in place, power for infusion pump drive mechanism 12 is generated by power generation circuit 8 (FIG. 1). The windings 86, 88 and 90, along with FETs 92, 94, and 96 form a fly-back circuit. The fly-back circuit is enabled by microprocessor 18 on line 33.

When it is desired to generate the voltage necessary for running pump drive mechanism 12, a positive voltage is supplied to winding 86 via line 33. This bias voltage is supplied to the gates of FETs 92, 94 and 96 after passage through winding 86. Once the enable signal is provided through windings 86, the three FETs are turned on and the V+ signal provided to winding 88 completes a circuit to common ground 71 through FETs 92, 94 and 96. Winding 88 then produces a varying field that affects windings 90 and 86. This varying field will cause an induced voltage to appear in windings 90 and 86. The negative feedback from winding 88 to winding 86 causes the FETs to effectively cut off. This breaks the circuit in primary winding 88 and causes the opposite varying field in winding 88.

Winding 90 is affected by also varying field of winding 88. Since the cycle is as described, winding 90 has an output which is oscillating. These oscillations appear as an AC signal in line 97. This AC signal is rectified by rectifier 98 and a pulsatory DC current is provided to the capacitor bank consisting of capacitors 100, 102, 104, 106, 108, 110 and 112.

Again referring to FIG. 4, the capacitor bank is power storage circuit 10 in FIG. 3. It will take approximately five seconds for the fly-back circuit to charge the capacitor bank to the proper level. Once the predetermined charge level of the capacitor bank is reached, the fly-back circuit will be disabled by removing the enable signal from line 33. Since the circuit includes zener diode 114, silicon controlled rectifier (SCR) 118 and diode 98, the charge on the capacitor bank remains on the capacitors until other operations take place which will cause it to be delivered to pump drive mechanism 12 as will be described subsequently.

In order to determine when the proper charge is on the capacitor bank, comparator 124 of sensing system 16 is used. V-1 signal 62 is directed to the inverting input and the voltage on line 115 is directed to the non-inverting input. Line 115 is also connected to the capacitor bank through pump mechanism 12 and zener diode 114.

As the charge is being built up in the capacitor bank, it is applied to zener diode 114 in the reversed direction. Zener diode 114 will break down at a certain voltage level. When this break down takes place, the voltage value at the non-inverting input to comparator 124 will increase.

In order to provide voltage level to comparator 124 via line 115, resistor 116 is placed in a circuit so that there will be a voltage drop across it. As the breakdown of zener diode 114 takes place, the voltage level, caused by the voltage drop across resistor 116, will cause a rise in the voltage at the non-inverting input of comparator 124. As the voltage applied to the non-inverting input of comparator 124 reaches a value greater than the value of V-1 62, the logic output of comparator 124 will change from a logic "0" value to a logic "1" value which is input input to microprocessor 18 via line 29. This logic "1" value signal on line 29 will cause microprocessor 18 to stop the output of the enable signal on line 33 for running the fly-back circuit previously described. Thus, the fly-back will be turned off and the proper level of stored charge is available in the capacitor bank for driving pump mechanism 12. Once charge is stored in the capacitor bank, the battery or primary power source 52 is no longer used for the fly-back charging circuit.

In order to deliver the charge stored in the capacitor bank to the pump drive mechanism, a signal must be received from microprocessor 18. When the software of the apparatus of invention determines that a pump stroke is needed the above charging sequence is completed and a fire signal is input to SCR 118 as a logic "1" signal via line 31. This signal will turn the SCR on and connect the output of pump drive mechanism 12 to ground. This provides a path for delivering the charge stored in the capacitor bank to the solenoid winding in pump drive mechanism 12. The pump drive mechanism is a magnetic solenoid type apparatus. When the charge is delivered, it will cause pump drive mechanism 12 to drive the pump and cause pumping of the desired fluid to the user.

The apparatus of invention checks to see if the charge time for the capacitor bank takes less than one second. If less than a second charging time takes place, the apparatus will recognize a false charging condition and will assume that there is a dead battery condition. This is one method to determine if the primary battery is dead.

The method in which a low battery condition is sensed is by use of comparator 122. This comparator has inputs from V-1 signal 62, which is input to the inverting input of comparator 122, and V-2 signal 64, which is input to the non-inverting input of comparator 122. The circuit is so configured that the initial condition V-1 signal 62 is greater than V-2 signal 64. As primary power source 52 has its charged depleted, V-1 will decrease faster than V-2. V-1 will fall below the V-2 at the point which is indicative of a low battery condition. Therefore, when the low operating point is reached, the output of comparator 122 will be a logic "1" value which is input to microprocessor 18 via line 27. There will be a display of this condition on LCD 40. This will also cause an output by tone transducer 22, after processing by the logic circuitry comprised of NOR Gate 128, capacitor 131, resistor 130 and 132 and NOR Gate 134 of the signal output microprocessor 18 on line 17. The actual operation of this circuitry will be described subsequently.

Again referring to FIG. 4, the method of driving tone transducer 22 is accomplished by microprocessor 18, NOR Gate 128, capacitor 131, resistors 130 and 132, and NOR Gate 134. NOR Gate 134 is the controlling gate for providing an input tone transducer 22. NOR Gate 128, capacitor 131, resistor 130 and resistor 132, comprise a self oscillating R/C circuit.

The output on line 17 from microprocessor 18 is normally a logic "1" value. When the output is desired from tone transducer, the output from microprocessor 18 on line 17 is a logic "0" value. Since the normal output is normally a logic "1" value, the output of NOR Gate 134 is a logic "0" value regardless of the condition of the self-oscillating circuit. When both inputs to NOR Gate 134 are logic "0" values, the output will be a logic "1" value. This will take place when a logic "0" value is output from microprocessor 18 on line 17 and when the output of the oscillator circuit is a logic "0" value. The logic "1" value output of NOR Gate 134 causes the oscillator circuit to oscillate between a logic "0" and a logic "1" each time the oscillator output assumes a logic "0" value. The tone transducer 22 will receive the oscillating signal and provide an audio output as per the logic "1" value output of NOR Gate 134.

The actuator means previously described are T button 30, A button 24, B button 26 and M button 28. These buttons connect to microprocessor 18 through connector board 55. The buttons are used for various functions. The main purpose of the buttons are to change program parameters and to cause the display of parameter values on LCD 40. A description of the buttons will be set forth subsequently.

The apparatus as previously indicated has a high pressure switch which is used to indicate when the fluid reservoir is empty, or when there is a problem with the pump mechanism such that plunger 5' (FIG. 1) cannot be driven into fluid reservoir 5 (FIG. 1), or when no fluid is being pumped when pumping is directed.

Referring to FIG. 4, high pressure switch 103 has a first terminal connected to the input of pump drive mechanism 12 through resistor 101 and a second terminal connected to ground. When the switch 103 is opened, the apparatus operates in the normal manner: the fly-back will charge the capacitor bank; and, when a fire signal is output from microprocessor 18 to SCR 118, the charge on the capacitors will be delivered to the pump drive mechanism 12.

However, when fluid reservoir 5 (FIG. 1) is empty or plunger 5' (FIG. 1) is obstructed and cannot cause pumping of fluid from the fluid reservoir, high pressure switch 103 will be closed as previously described. When this happens, line 97 (which is input to pump drive mechanism 12) and the capacitor bank are shorted to ground through resistor 101 and high pressure switch 103. Therefore, once switch 103 is closed, when the fly-back circuit is enabled to charge the capacitor bank, the current induced in winding 90 will be shorted to ground. There will not be charging of the capacitor bank, so the output of comparator 124 will not assume a logic "1" value within the time window for charging the capacitor bank once the fly-back is enabled.

If the capacitor bank, as seen by capacitor 124, is not charged to the proper level within approximately 12 seconds, microprocessor 18 determines that there is a problem with the apparatus. Microprocessor 18 enters an alarm state indicating the apparatus is not pumping fluid when directed. The alarms associated with this state are both audio and visual (on the LCD).

Actuation of the buttons will interrupt the normal operating routine of the microprocessor. The change in programming caused by actuation of the buttons will affect the operation of the apparatus. This interrupt is caused through FET 138.

When the primary power source is in place, the gate of FET 138 receives a positive gate voltage and the FET is turned on. When this takes place, pull-up resistor 136 will be defeated causing a logic "0" value at point 135 when one or a combination of buttons are actuated. This logic "0" value is input to microprocessor 18 via line 37. This input on line 37 will cause scanning of the button I/O lines 19, 21, 23 and 25 by microprocessor 18. Once microprocessor 18 determines which button or buttons have been actuated, it will take appropriate action and update memory with a new parameter value and/or cause the microprocessor to output from memory certain parameters which will be displayed on LCD 40.

The timing for the apparatus is carried out by a 32768 Hz clock using crystal 148. The frequency is divided down internally by the microprocessor and causes proper timing for apparatus.

The apparatus of invention has certain safeguards which are necessary to prevent inadvertent or unauthorized changing of the program parameters for the user. The main safeguard is that there is a circuit external to microprocessor 18 that must be activated before certain programming, e.g., setting maximum limits for the apparatus, can be effectuated. The circuit contains a switch which must be closed before such changes can be accomplished.

Referring to FIG. 4, reed switch 159 is normally in an open condition. One terminal of reed switch 159 is connected to a V+ voltage through pull-up resistor 157 and to I/O port line 161. The second terminal of reed switch 159 is common ground 71.

In the open condition, the voltage on line 161 is a logic "1" value. However, when an external device causes reed switch 159 to close, the voltage in line 161 will assume a logic "0" value and enable microprocessor 18 to receive the desired new programming.

Again referring to FIG. 4, the apparatus is configured so that the same interconnecting lines between microprocessor 18, address latch 36 and memory 34 are used as a multiplexed address bus and data bus. The timing and circuitry of the apparatus of invention are set up so that during the period that the interconnecting lines used as the address bus, memory 34 is disabled so that there is no data output on the interconnecting lines. Likewise, when the data is being output from memory 34 and the lines are used as the data bus, address latch 36 latches the previous address and the address latch is not affected by information from the data bus.

In order to carry this out, there must be an explanation of the logic circuitry (referred to as memory enable circuit 32 in FIG. 3) involving NOR Gate 158, NOR Gate 156, and flip-flop 162. In conjunction with describing the logic circuitry, the timing diagrams for bus control signals of microprocessor 18 will be described.

Figures 5, 6:
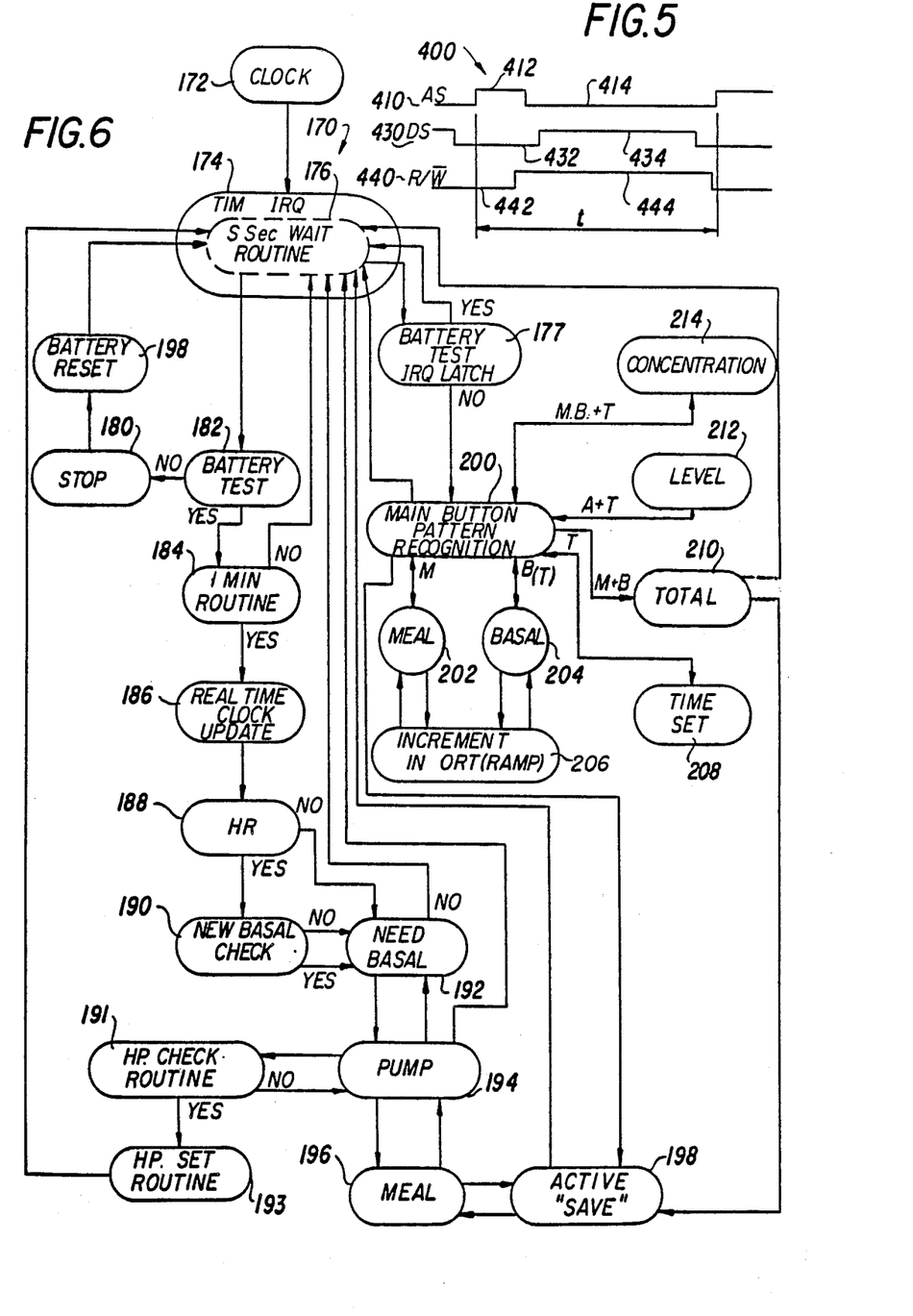
FIG. 5 shows the timing diagram for the bus control signals for the microprocessor of FIG. 4.
FIG. 6 shows a general flow diagram of the software of the apparatus of the invention.

Referring to FIG. 5, the timing diagrams AS signal 410, DS signal 430, and R/$\overline{\text{W}}$ signal 440 are shown generally at 400. These are the bus control signals from microprocessor 18. The cycle period is labelled time "t". The relationship between AS signal 410, DS signal 430 and R/$\overline{\text{W}}$ 440 is shown.

Referring to FIGS. 4 and 5, at the beginning of the cycle, when DS signal 430 has a logic "0" value, it is input to the tied inputs of NOR Gate 158 via line 15. This causes the output of that logic gate to assume a logic "1" value, which is input to flip-flop 162. This logic "1" value signal will reset flip-flop 162 and the $\overline{Q}$ output of flip-flop 162 will assume a logic "1" value. This logic "1" value is input to the chip enable ($\overline{CE}$) and output enable ($\overline{OE}$) inputs to memory 34. Since the $\overline{CE}$ and $\overline{OE}$ inputs are negative/true, the logic "1" value input to each will render chip 34 disabled and no outputs will be available from memory 34. At the same time, AS signal 410 with a logic "1" value is input to address latch 36. This input allows address latch 36 to receive inputs from the address bus lines.

Continuing through the cycle of period "t", R/$\overline{W}$ signal 440 assumes a logic "1" value prior to AS signal 410 assuming a logic "0" value at 414. When R/$\overline{W}$ signal 440 assumes a logic "1" value, the input to the D input to flip-flop 162 changes from a logic "0" value to a logic "1" value. The clock signal for flip-flop 162 is the output of NOR Gate 156. The inputs to NOR Gate 156 are tied and the output of oscillator circuit of crystal 148 previously described. When the oscillator circuit output transitions from a logic "1" value to a logic "0" value, the output of NOR Gate 156 will change from a logic "0" value to a logic "1" value. The positive edge will clock flip-flop 162. However, since DS signal 430 remains a logic "0" value at 432, flip-flop will remain reset and the clocking of flip-flop 162 will have no effect on the $\overline{Q}$ output of flip-flop 162.

When the timing of the cycle reaches the point where DS signal 430 assumes a logic "1" value 434, the output of NOR Gate 158 will assume a logic "0" value which is input to the reset input of flip-flop 162. When this happens, flip-flop 162 will no longer be held reset. Since R/$\overline{W}$ signal 440 is a logic "1" value at 444, the logic "1" value loaded into the D input of flip-flop 162 will upon clocking cause the $\overline{Q}$ output of flip-flop 162 to assume a logic "0" output. This logic "0" value is input to the $\overline{CE}$ and $\overline{OE}$ inputs of memory 34 which are both negative/true inputs. This will enable the memory and cause output from memory 34. The lines are now used as data bus lines for input to microprocessor 18 from memory 34. Therefore, the output from memory 34 is input to microprocessor 18 for processing in accordance with the software commands. Just prior to this action, the AS output 410 transitions to a logic "1" value which causes latching of the address values. These values are supplied to memory 34 via address lines during the data retrieval interval.

Referring to FIG. 4, the components of the apparatus of invention have inputs to connector board 55. This connector board processes the information and provides inputs to LCD 40 to display certain information indicative of the inputs to connector board 55.

Referring to FIG. 6, a flow diagram of the software of the apparatus of the invention is shown at 170. The apparatus of invention operates on two levels. The first level is a sleep state and the second level is an active state. The apparatus operates in these two states to conserve the batteries and give them extended life.

The timing for the apparatus is controlled by quartz clock 172. The basic operation of this low level system centers around the interrupt routine 174 having 5 second wait subroutine 176 contained therein. The apparatus is constructed so that the apparatus will be woken up every 5 seconds to check certain conditions, update the apparatus clock, control the output functions of the apparatus and return to the sleep state. This 5 second time period is the minimum inactive interval for the apparatus. The only actions which can take place outside of the 5 second wake up subroutine are caused by actuation of the buttons causing the apparatus to shift to an "active" state, thereby invoking main button pattern recognition subroutine 200, or the reset the battery test IRQ interrupt subroutine 177, which is generated each time the battery test routine 182 is entered. These two interactive portions of software will be described.

Again referring to FIG. 6, when the subroutine associated with main button pattern recognition 200 is initiated, by actuation of one or a combination of buttons, the apparatus leaves the 5 second wait subroutine and enters the main button pattern recognition subroutine 200 to determine which button has been actuated and take the appropriate action. The buttons can be actuated alone or in combinations. Each subroutine associated with button activation will be described subsequently.

When M, B and T buttons are actuated simultaneously, the main button recognition pattern is entered. When the button pattern is recognized the apparatus will enter concentration subroutine 214. When this happens, the concentration of the fluid in the fluid reservoir (not shown) will be displayed on LCD 40. If this is the only button actuation, a short period of time after release of the buttons of the apparatus will return to the 5 second wait subroutine. If it is desired to change the concentration of the fluid being pumped to the user first, the reed switch must be closed by an external device, then the M, B and T buttons are actuated again simultaneously. The concentration of the fluid will again be displayed on the LCD. The B button must be actuated to change to the desired concentration. When the desired concentration is reached, the A button is actuated which will store the new concentration parameter value in memory. A short period of time after storage of the new parameter value, the apparatus will return to the 5 second wait subroutine 176. This action will also cause all previous program parameters to assume zero values.

When the A and T buttons are actuated simultaneously, the apparatus will enter the main button recognition pattern 200. After this button pattern is recognized, the apparatus will enter the level subroutine 212. This results in a display indicative of the units of fluid remaining in the fluid reservoir. A short period of time after release of the buttons, the apparatus will return to a 5 second wait routine 176.

It is always necessary to restore the apparatuses full fluid level condition every time a new fluid reservoir is placed in the apparatus. This is done by actuating the A and T buttons simultaneously, releasing the A and T buttons and reactuating and holding the A button until the full level is indicated. When this value is indicated, the A button is released and the full value is stored in memory. The apparatus will then return to a 5 second wait subroutine 176.

When the M and B buttons are activated simultaneously, the apparatus will enter the main button pattern recognition routine 200. After the button pattern is recognized, the apparatus will enter total subroutine 210. The total value is the amount of fluid in units pumped from the fluid reservoir since the previous midnight. This amount will be displayed on the LCD. After a short period of time, the apparatus will return to 5 second wait subroutine 176.

When the apparatus is in the total subroutine 210 and the A button is actuated, the apparatus will go into a standby mode. In this mode, the apparatus is powered but no internal function takes place other than timekeeping and maintaining RAM. This is used, when the user may wish to disconnect the apparatus to take a shower or other similar action where there is no need for the apparatus of invention for an extended period of time. When this activity is over, the M and B button actuation is repeated and the apparatus returns to the total subroutine 210. After actuation of the A button, the apparatus will return to normal operation within 5 second wait routine 176.

When the T button is pressed alone, the apparatus will enter the time set subroutine 208, which is used for setting the time, after recognition by main button pattern recognition subroutine 200. The time will be displayed on the LCD by this first activation. To correct the time, the T button is actuated until the proper time is displayed. After this, the A button is actuated to store the new parameter in memory and the apparatus will return to the 5 second wait routine 176.

When the B button is actuated alone, the apparatus will enter the main button pattern recognition subroutine 200 and then basal rate subroutine 204. This basal rate will then be displayed on the LCD. If nothing else is done, after a period of time, the apparatus will return to 5 second wait routine 176. If it is desired to change the basal rate, the B button is held in the activated position and the basal rate value will increase. When the desired value is reached, the button is released and the A button is activated which stores the value in memory and the apparatus will return to 5 second wait routine 176.

There are a maximum of four basal rate profiles into which any 24 hour period can be divided. In order to index to any specific profile the T button is used. Once in one of the basal rate profiles indexing to subsequent profiles is carried out by actuating the T button successively. When the desired profile is checked or changed, the apparatus will return to the 5 second wait routine 176 after release of the A or T button depending on whether the basal rate profile was changed or checked, repectively. The reed switch must be actuated in order to change both the time and rate parameters of a basal profile. Otherwise, only the rate parameter can be changed. No permanent change to any basal rate is accomplished unless stored by actuation of the A button.

When the M button is actuated alone, as with the other buttons, the main button pattern recognition subroutine 200 is entered and then the meal basal rate subroutine 202 is entered once the actuated button is recognized. The meal rate 202 is not automatically delivered. This must be specially done each time a meal dosage is to be delivered to the user. When a meal dose is needed, the M button is actuated and a "0" value is displayed on the LCD. The M button is then held actuated until the value on the LCD ramps up to the desired value by subroutine 206. When this desired value is reached, the M button is released and the A button is actuated. This will cause the apparatus to deliver the meal dosage from the apparatus to the user. At the completion of the delivery of the meal dosage the apparatus will return to the 5 second wait routine 176.

The following will be a description of the software associated with the 5 second wait subroutine 176. When the apparatus is awakened at the end of every 5 second period, it leaves 5 second wait subroutine 176 and enters battery test subroutine 182. If the test is not satisfactory, (primary batteries not present) the apparatus will go to Stop State 180 and go to sleep state. Only after reinsertion of batteries will the apparatus wake up and battery reset condition 198 be completed and the apparatus will return to the 5 second wait subroutine.

If the battery test is successful, the apparatus will count out 12, 5 second interrupts and then enter the 1 minute subroutine 184. In this timekeeping mode, the apparatus only carries out or activates other subroutines at 1 minute or 1 hour intervals. After 1 minute routine 184 is entered, the real time clock 186 is updated by 1 minute. After 60 one minute updates, the software enters hour subroutine 188. The hour subroutine is for checking changed conditions of the apparatus, change in the basal profile 190, and for updating real time clock 186 by 1 hour.

If there is a need for basal stroke, Need Basal subroutine 192 is entered either from new basal check subroutine 190 or from hour subroutine 188.

If a basal stroke is not needed, the apparatus will return to 5 second wait subroutine 176. If a basal stroke is needed, the apparatus will enter pump routine 194. However, before the routine causes any pumping, the apparatus enters HP (high pressure) check routine 191 to determine if the high pressure switch is closed. If it is closed, the apparatus will enter HP set routine 193, which causes certain alarm conditions to be set and the apparatus will return to 5 second wait subroutine 176. If when checked the HP switch is not closed, the apparatus will return to pump routine 194 and cause pumping of fluid from the apparatus.

FIGS. 7, 8, 9a, and 9b show the engagement/disengagement means for lead screw 242 for the apparatus of invention. The lead screw is driven by pump drive mechanism 12. Engagement/disengagement means 220 contacts plunger 5' which is part of the pumping system of the apparatus. By forcing plunger 5' into reservoir 5, fluid is forced from the fluid reservoir to the user.

Figures 7, 8:
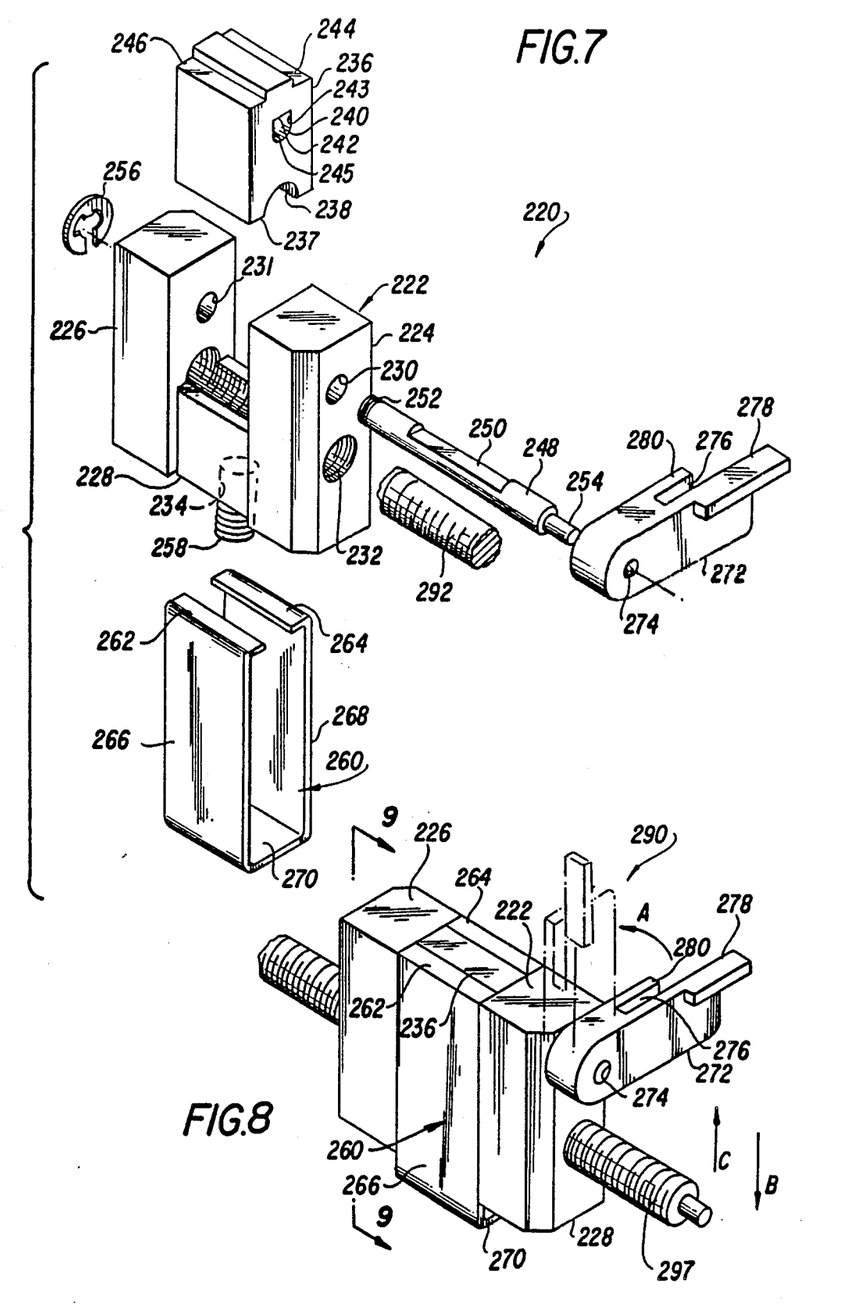
FIG. 7 shows an exploded view of the engagement/disengagement means of the apparatus of invention for engaging and disengaging the lead screw.
FIG. 8 shows the assembled engagement/disengagement means of FIG. 7.

Referring to FIG. 7, an exploded view of engagement/disengagement means for lead screw 292 is generally shown at 220. The apparatus has a "U" shaped body 222. The body is comprised of first or center section 228 having second section 224 disposed perpendicular to a first end of first section 228 and a third section 224 disoposed perpendicular to the second end of first section 228 with the second and third sections being parallel to each other.

Second section 224 and third section of 226 have bores 230 and 231 disposed therethrough, respectively. These bores are also in alignment. Another bore 232 is disposed through section 224, 226 and 228. This bore is for receiving therethrough lead screw 292. However, only a half diameter is cut into a surface of center section 228 such that lead screw 292 would have half its diameter exposed when it is disposed through bore 232.

A third bore 234 is disposed partially through center section 228. This bore enters from the bottom surface of center section 228. This bore is used for disposition of spring 258, which will be described subsequently.

Engagement/disengagement means 220 has engaging member 236 which is of a size of that it will fit in the area between parallel second and third sections 224 and 226, respectively, of the "U" shaped body member 222. Bottom surface 237 of the engaging member 236 has a half diameter cut longitudinally in it. This half diameter has threads 238, which are matched to the threads of lead screw 292. It is the engagement/disengagemnet of these threads which allows the engagement/disengagement means to operate in the desired fashion with lead screw 292.

Engaging member 236 has a first bore 240 disposed through it. The cross-sectional shape of bore 240 has elongated sides 243 and 245 to allow interaction between member 236 and a shaft disposed therein. Bore 240 also has a flat surface 242 disposed at the top of the bore. This bore is for receiving a portion of shaft 248 when means 220 is assembled.

Shaft 248 has a relieved portion having flat surface 250. The relieved portion is at least the length of bore 240 of engaging member 236. The operation of the relieved portion and the engaging member 236 will be described subsequently.

Shaft 248 has a first end 252 which receives "E" ring 256. Shaft 248 is disposed through bores 230, 240 and 231 when means 220 is assembled. Shaft 248 has a second end having a reduced diameter member 254. This second end receives lever actuator means 272 such that bore 274 of the lever receives reduced diameter shaft 254 therethrough. Lever actuator means 272 has members 280 and 278 which are disposed that slot 276 is formed between them for receiving a portion of plunger 5' (FIG. 2) of the pump mechanism for causing the pumping fluid from the fluid reservoir.

Engaging/disengaging member 220 has a bracket member 260. Bracket member 260 has parallel side members 266 and 268 which are joined by bottom member 270. The side members are disposed perpendicular to bottom member 270. On the ends of each side members 266 and 268, opposite the points of attachment to bottom member 270 are disposed lip members 262 and 264. These are disposed perpendicular to the respective side members, parallel to bottom member 270 and toward each other but their distal ends are spaced apart.

When disposed on the apparatus, the bottom member 270 is biased against spring 258 disposed in bore 234 of first section 288. Side members 266 and 268 are disposed along opposite sides of body 222 with engaging member 236 inserted therein and lip members 262 and 264 are disposed on sections 246 and 244 of engaging member 236 holding the bracket in place. This configuration causes spring 258 to bias the bracket in downward direction B. This will in turn bias engaging means 236 which is in contact with bracket 260 toward lead screw 292 disposed in bore 232.

Referring to FIG. 8, an elevated view of the assembled apparatus is shown disposed on a lead screw 292. Lever actuator means 272 is shown in phantom rotated in a direction A. The resultant actions of engagement/disengagement means 220 because of such rotation will be described in conjunction with the disclosure of FIGS. 9A and 9B.

Figure 9A:
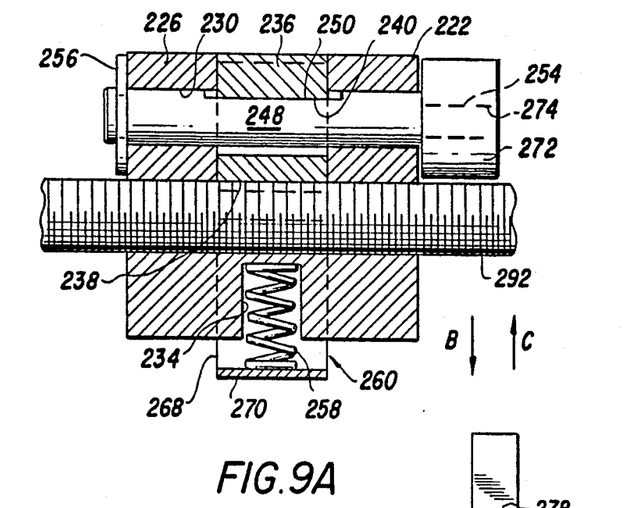
FIG. 9A shows a cross-sectional view of the engagement/disengagement apparatus at 9—9 of FIG. 8 with the pump driver in the normal position.
Figure 9B:
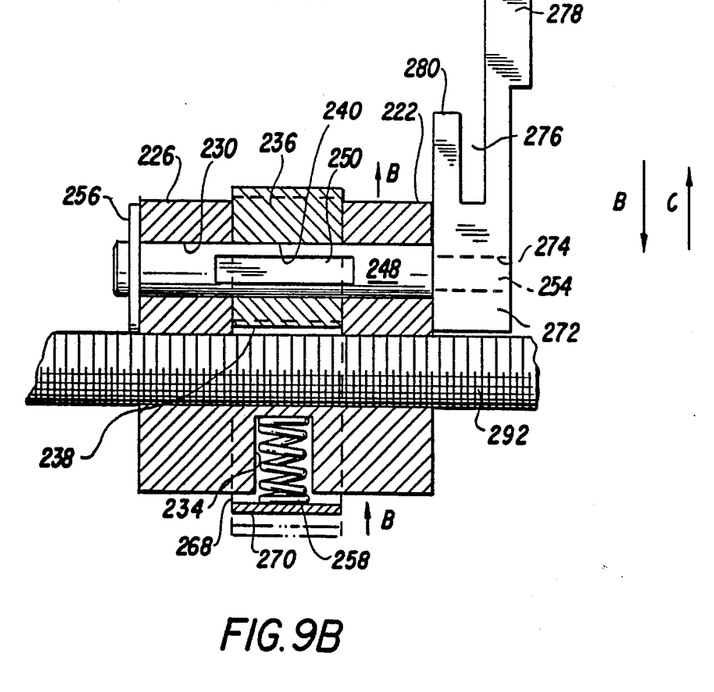
FIG. 9B shows a cross-sectional view of the engagement/disengagement means at 9—9 of FIG. 8 with the pump driver rotated in a first direction.

Referring to FIG. 9A, a cross-sectional view of engagement/disengagement means 220 shown in FIG. 8 at 9—9 of FIG. 8. Referring to FIG. 9B, a cross-sectional view of engagement/disengagement means 220 shown in FIG. 8 at 9—9 with the lever actuator means 272 rotated in direction A.

Again referring to FIG. 9A, when lever actuator means 272 is down, as shown in solid lines in FIG. 8, shaft 248 has the relieved portion having flat surface 250 facing up. In this position, flat surface 242 of bore 240 is biased down against the relieved portion flat surface 250 by biasing spring 258 that biases engaging member 236 in a downward direction B via bracket member 260. This will cause threaded portion 238 of engaging member 236 to engage the threads of lead screw 292, thereby engaging engagement/disengagement means 220 such that means 220 and the lead screw 292 are in a screw/nut relationship.

Referring to FIG. 9B, when it is desired not to engage engagement/disengagement means 220 from lead screw 292 such that the means 220 will freely slide up and down lead screw 292, lever actuator 272 is rotated in direction A, as shown in FIG. 9B. When this takes place, relieved portion having flat surface 250 of shaft 248 is rotated out of contact with the flat portion 242 of bore 240 of engaging member 236. This will cause flat portion 242 of bore 240 to now ride on the outside diameter of shaft 248. This will cause the engaging member 236 to move in direction C in opposition to biasing spring 258. This will drive the threads 238 of engaging member 236 out of engagement with the threads of lead screw 292. The means 220 can now freely slide up and down lead screw 292. Engagement/disengagement means 220 is configured in this manner so that when the fluid reservoir is empty or must be changed for some other reason, the lever actuator 272 can be lifted or rotated out of engagement with the threads of lead screw 292 and the means 220 can be repositioned to receive the new reservoir and plunger.

Referring to FIGS. 10, 11, 12 and 13, pump drive mechanism 12 for driving lead screw 292 for pumping fluid from the fluid reservoir 5 is shown.

Figure 10:
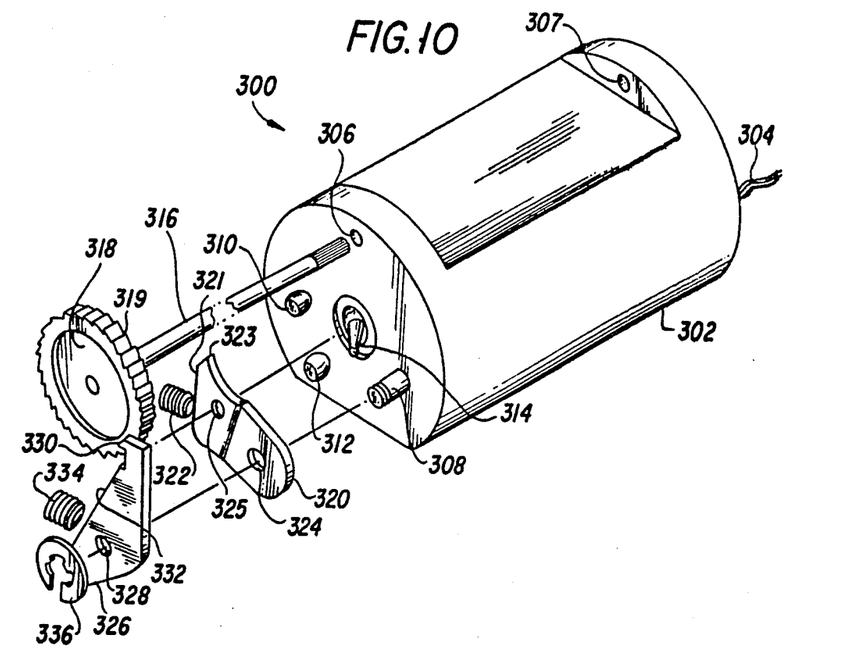
FIG. 10 shows a partially exploded view of the solenoid drive means of the apparatus.

Referring to FIG. 10 an exploded view of the mechanism is generally shown at 300. The drive mechanism 300 is a solenoid drive apparatus for converting electrical energy into the mechanical energy. Mechanism 300 has outer housing 302 and leads 304 for receiving the output from power storage unit 10 shown in FIG. 3. The housing also has bores 306 and 307 for receiving therethrough drive shaft 316 for driving lead screw 292 through a coupling (not shown). Attached to an end of drive shaft 316 is ratchet wheel 318 having teeth 319 disposed around the periphery. Housing 302 has disposed at one end spring stops 310 and 312. These are stops for springs 322 and 334, respectively. There is also a post 308 which is for slidable attachment of first pawl 320 and rotatable attachment of second pawl 326, respectively. Slot 324 of first pawl 320 is disposed on post 308 to allow for the linear movement of the pawl.

Pawl 320 works in conjunction with pawn 314, which extends from the interior through the first end of housing 302, and spring 322. This combination drives ratchet wheel 318 and resets pawl 320 as will be described. Pawl 326 works in conjunction with driven pawl 320, spring 334 and ratchet wheel 318. Pawl 326 is an anti-backlash pawl, as will be described subsequently. Finally, E-ring 336 is disposed on the end of post 308 to hold pawls 320 and 326 in place when the apparatus is assembled.

Figure 11:
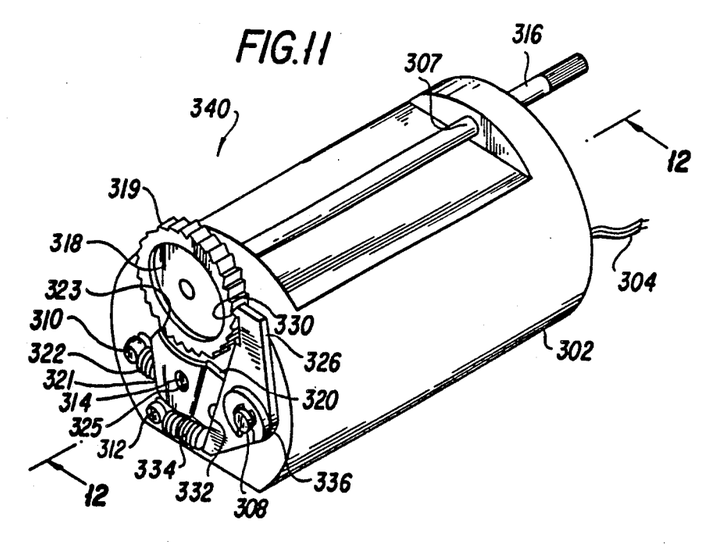
FIG. 11 shows an assembled view of the solenoid drive means of the invention shown in FIG. 10.

Referring to FIG. 11, the assembled solenoid drive mechanism 300 is shown generally at 340. The operation of the solenoid drive mechanism 300 will be described referring to FIGS. 11, 12 and 13.

Figure 12:
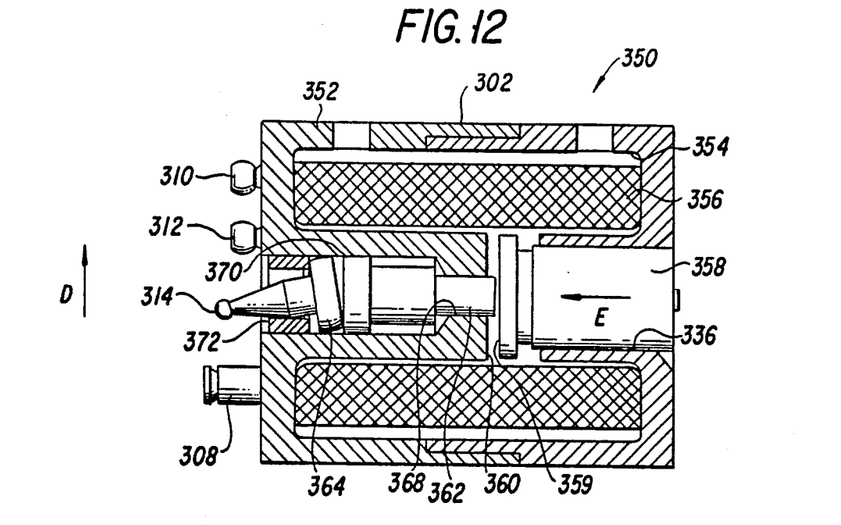
FIG. 12 shows a cross-sectional view of the solenoid drive means of the invention shown at 12—12 of FIG. 11.

Referring to FIG. 12, a cross-sectional view of the mechanism is shown generally at 350. The housing has two sections. First section 352 and second section 354 meet in a mating relationship.

Disposed in opening 353 within housing 302 is solenoid winding 356. Storage unit 10 (FIG. 3) will deliver its charge to solenoid winding 356 and cause generation of the field which causes solenoid armature 358, disposed in bore 336 of second section 354 of housing 302, to be driven in direction E. Surface 359 of solenoid armature 358, when the charge is delivered, will be driven toward surface 360 of first section 352. Surface 360 in fact acts as a stop for surface 359.

When armature 358 moves in direction E, it will drive push rod 362 having a first portion disposed in bore 368 and a second portion disposed in a bore 370 in direction E since the tip of push rod extends into bore 336. This will cause the end of pawn 314 to move in direction D.

Figure 13:
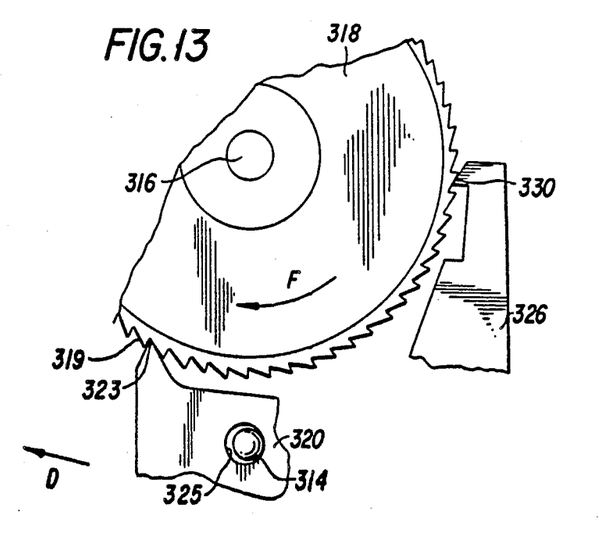
FIG. 13 shows a partial view of the ratchet means and pawls which engage the ratchet means of the solenoid drive means shown in FIG. 11.

Referring to FIG. 13 when the above happens, pawl 320 having the end of pawn 314 disposed in bore 325 will also be driven in direction D. Since tip 323 of pawn 320 engages teeth 319 of ratchet wheel 318, the ratchet wheel will be driven in direction F. Likewise tip 330 of pawl 326, which in a normal engagement position prior to movement of pawl 320, is disposed one half the distance along one of the teeth 319 of ratchet wheel 318, will be caused to overcome that one tooth when pawl 320 is driven in direction D. Pawl 326 with tooth 330 acts as an antibacklash device. Therefore, because of tooth 330 of pawl 326 the only backward movement of ratchet wheel 318 will be of a half a tooth distance in a direction counter to direction F.

Referring to FIG. 11, when tip 323 engages teeth 319 of ratchet wheel 318 and driven in a direction D by pawn 314 disposed through a bore 325 of pawl 320, spring 322 will be biased by pawn 320. When the charge is depleted, spring 322 will force pawl 320 and pawn 314 back to their original positions. Likewise, once tip 330 of pawl 326 is lifted over a tooth, spring 334 will extend and push it back to its original position, however tip 330 will be against the next tooth of ratchet wheel 318. This ratcheting will take place each time the charge is delivered to the solenoid windings.

The terms and expressions which are employed here are used as terms of description and not of limitation. There is no intention in the use of such terms and expressions of excluding equivalence of the feature shown, and described, or portions thereof, it being recognized that various modifications are possible in the scope of the invention as claimed.

We claim:

1. A programmable fluid pumping apparatus comprising:
    power producing means for supplying power to said apparatus comprising:
      a first power source for supplying power to said apparatus, and
      a second power source for supplying power to a portion of said apparatus only when said first power source cannot supply adequate power to said apparatus;
    a first circuit means responsive to said power producing means for assisting said power producing means in producing necessary power levels;
    a second circuit means responsive to an output of said power producing means for generating sufficient power for driving a pump drive means;
    a third circuit means responsive to an output of said second circuit means for storing power generated by said second circuit means;
    said pump drive means being responsive to an output of said third circuit means;
    pump means mechanically connected and responsive to said pump drive means for pumping fluid from a fluid reservoir;
    a first sensing means responsive to a stored power level of said third circuit means for determining when said stored power level equals or exceeds a predetermined value;
    a second sensing means responsive to a power level of said power producing means for determining when the power level of said power producing means has dropped below a predetermined value;
    processing means responsive to and interactive with said power producing means, first circuit means, second circuit means, third circuit means, first sensing means, and second sensing means for controlling the operation of said pumping apparatus;
    a plurality of actuator means interactive with said processing means for controlling operating parameter values utilized by said processing means;
    memory means interactive with and responsive to said processing means for storing and providing said operating parameter values used by said processing means; and
    indicator means responsive to said processing means for providing selective indications of the operating status or condition of said apparatus.

2. The apparatus as recited in claim 1 wherein said first circuit means is responsive to said second power source to assist said second power source to generate sufficient power to power at least a portion of said memory means.

3. The apparatus as recited in claim 1 wherein said plurality of actuator means include at least a first, second, third and fourth switch means.

4. The apparatus as recited in claim 3 wherein said first switch means when actuated alone is control means for indicating or changing time settings for the apparatus.

5. The apparatus as recited in claim 3 wherein said third switch means when actuated alone is control means for indicating or changing a basal rate of fluid to be pumped for a predetermined period.

6. The apparatus as recited in claim 3 wherein said fourth switch means when actuated alone is control means for indicating or changing a meal rate of fluid to be pumped for a predetermined meal period.

7. The apparatus as recited in claim 3 wherein actuation of said second switch means subsequent to actuation of either said first, third or fourth switch means singularly or in combination causes changing of a parameter value in said memory means.

8. The apparatus as recited in claim 3 wherein simultaneous actuation of the first, third and fourth switch means indicates the concentration of fluid being pumped from said apparatus.

9. The apparatus as recited in claim 3 wherein simultaneous actuation of said first and second switch means indicates the level of fluid remaining in said fluid reservoir.

10. The apparatus as recited in claim 9 wherein actuation of said second switch means subsequent to actuation of said first and second switch means resets a level parameter value in said memory means to a preset value.

11. The apparatus as recited in claim 3 wherein actuation of said third switch means followed by actuation of said first switch means enables a specific basal fluid pumping rate to be selected from a plurality of basal pumping rates, said plurality of basal pumping rates being sequentially made available for selection by successive actuation of said first switch means.

12. The apparatus as recited in claim 3 wherein simultaneous actuation of said third and fourth switch means causes said indicator means to display the amount of fluid dispensed from the apparatus within a predetermined time interval.

13. The apparatus as recited in claim 12 wherein simultaneous actuation of the third and fourth switch means, followed by actuation of said second switch means, causes said apparatus to enter a standby mode of operation.

14. The apparatus as recited in claim 3 wherein the apparatus is responsive to an external control means for controlling access to at least one portion of the memory means for the purpose of changing and/or setting a parameter value in that portion of the memory means.

15. The apparatus as recited in claim 14 wherein actuation of certain sequences of said actuation means in combination with the external control means allows access to said portions of the memory means for the purpose of changing or setting said parameter values.

16. The apparatus as recited in claim 1 wherein said indicator means includes a display means and an audio tone generator means.

17. The apparatus as recited in claim 16 wherein said audio tone generating means is responsive to said processing means for generating audio tones indicative of certain conditions of the apparatus.

18. The apparatus as recited in claim 1 wherein said apparatus further comprises a third sensing means connected to said pump drive means for sensing when said pump drive means is unable to cause said pump means to pump fluid from said fluid reservoir.

19. The apparatus as recited in claim 18 wherein a condition sensed by said third sensing means includes an empty fluid reservoir.

20. The apparatus as recited in claim 18 wherein a condition sensed by said third sensing means includes a condition preventing said pump means from pumping fluid from said fluid reservoir when said fluid reservoir has fluid in said reservoir.

* * * * *